United States Patent
Takaya et al.

(10) Patent No.: US 11,116,464 B2
(45) Date of Patent: Sep. 14, 2021

(54) X-RAY DIAGNOSTIC APPARATUS AND IMAGE PROCESSING APPARATUS

(71) Applicant: Toshiba Medical Systems Corporation, Otawara (JP)

(72) Inventors: Mika Takaya, Otawara (JP); Shingo Abe, Nasushiobara (JP); Ko Fuchigami, Otawara (JP); Ryoichi Nagae, Nasushiobara (JP); Takuya Sakaguchi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 501 days.

(21) Appl. No.: 15/331,114

(22) Filed: Oct. 21, 2016

(65) Prior Publication Data

US 2017/0119332 A1    May 4, 2017

(30) Foreign Application Priority Data

Oct. 28, 2015 (JP) .............................. JP2015-211943
Sep. 2, 2016 (JP) .............................. JP2016-172072

(51) Int. Cl.
*A61B 6/02* (2006.01)
*A61B 6/00* (2006.01)
*A61B 6/12* (2006.01)

(52) U.S. Cl.
CPC ............... *A61B 6/504* (2013.01); *A61B 6/12* (2013.01); *A61B 6/4441* (2013.01); *A61B 6/465* (2013.01); *A61B 6/481* (2013.01); *A61B 6/487* (2013.01); *A61B 6/507* (2013.01); *A61B 6/5211* (2013.01)

(58) Field of Classification Search
CPC .. A61B 6/486; A61B 5/04; A61B 6/06; A61B 6/481; A61B 6/5211; A61B 6/54

USPC .......................................................... 378/62
See application file for complete search history.

(56) References Cited

U.S. PATENT DOCUMENTS

| | | | |
|---|---|---|---|
| 2011/0206183 A1* | 8/2011 | Tanaka | A61B 6/0457 378/62 |
| 2016/0022236 A1* | 1/2016 | Ohishi | A61B 6/481 600/431 |
| 2017/0119332 A1* | 5/2017 | Takaya | A61B 6/504 |

FOREIGN PATENT DOCUMENTS

| | | |
|---|---|---|
| JP | 60-220045 A | 11/1985 |
| JP | 2003-38477 | 2/2003 |
| JP | 2009-22733 | 2/2009 |
| JP | 2009-279331 | 12/2009 |

(Continued)

OTHER PUBLICATIONS

Japanese Office Action dated Jun. 30, 2020 in Japanese Patent Application No. 2016-172072, 4 pages.

*Primary Examiner* — Jon Eric C Morales
(74) *Attorney, Agent, or Firm* — Oblon, McClelland, Maier & Neustadt, L.L.P.

(57) ABSTRACT

An X-ray diagnostic apparatus according to an embodiment includes processing circuitry configured to acquire a plurality of X-ray images over time based on X-rays having passed through a subject injected with a contrast agent, to calculate a blood vessel region corresponding to an inflow path of the contrast agent leading to a predetermined position in the blood vessel region, based on a temporal transition of signal intensities of the contrast agent in the blood vessel region represented in the X-ray images, and to perform control to display the blood vessel region corresponding to the inflow path in a display mode that is different from that of a blood vessel region other than the inflow path on a display.

19 Claims, 9 Drawing Sheets

(56) References Cited

FOREIGN PATENT DOCUMENTS

| | | |
|---|---|---|
| JP | 2009-285121 | 12/2009 |
| JP | 2011-516108 A | 5/2011 |
| JP | 2012-5636 | 1/2012 |
| WO | WO 2014/162273 A1 | 10/2014 |

\* cited by examiner

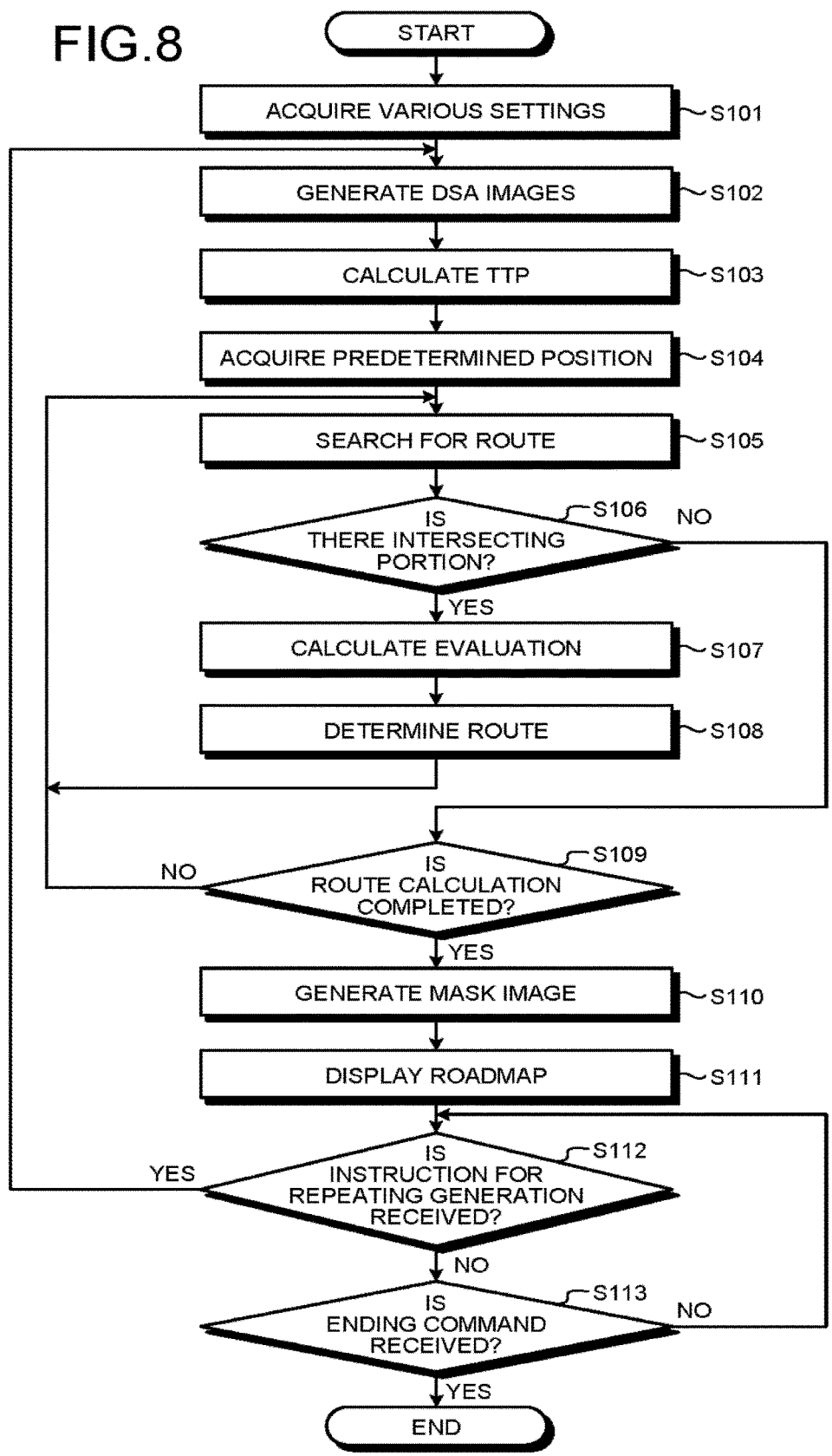

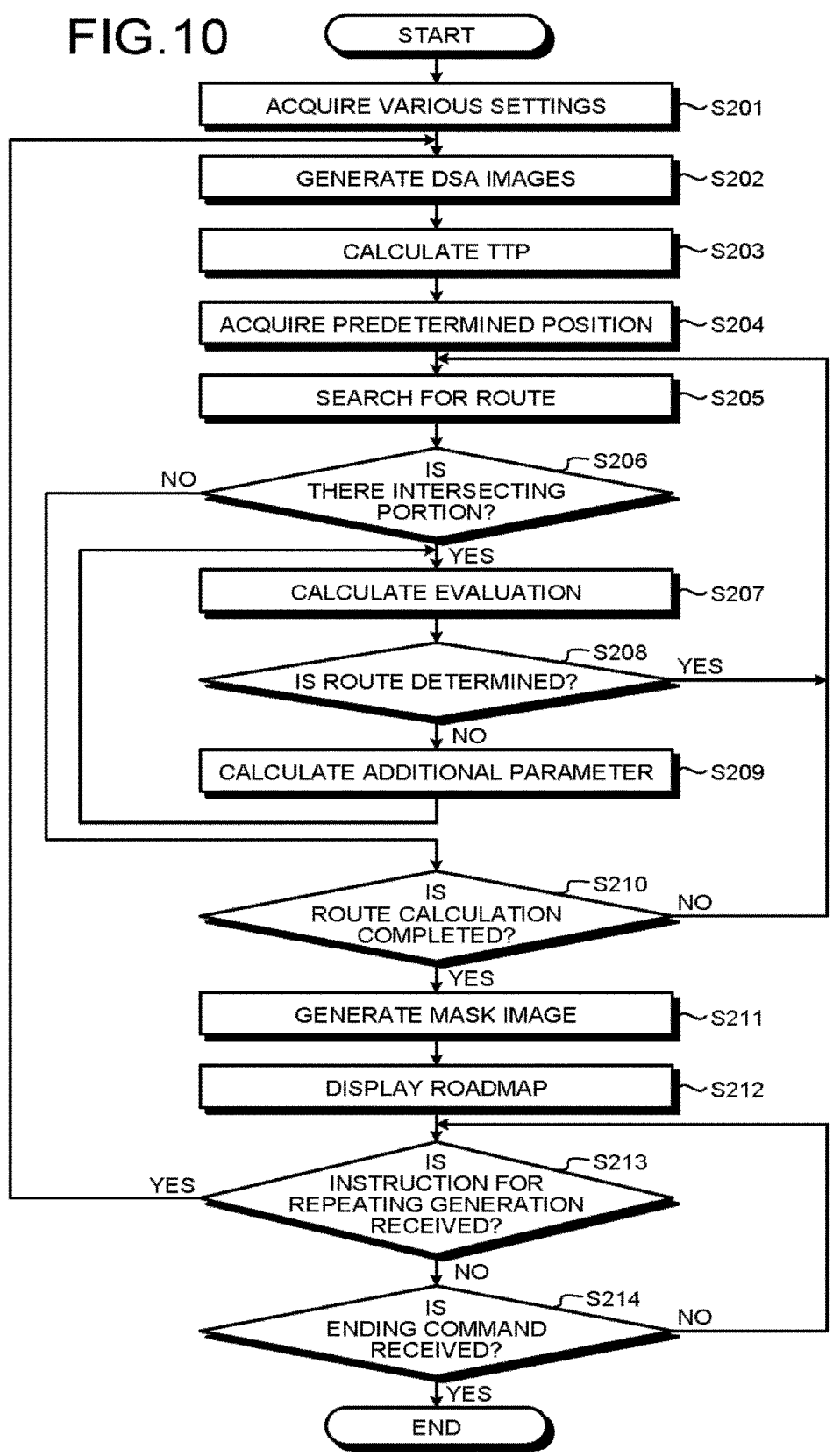

X-RAY DIAGNOSTIC APPARATUS AND IMAGE PROCESSING APPARATUS

CROSS-REFERENCE TO RELATED APPLICATIONS

This application is based upon and claims the benefit of priority from Japanese Patent Application No. 2015-211943, filed on Oct. 28, 2015; and Japanese Patent Application No. 2016-172072, filed on Sep. 2, 2016, the entire contents of all of which are incorporated herein by reference.

FIELD

Embodiments described herein relate generally to an X-ray diagnostic apparatus and an image processing apparatus.

BACKGROUND

Interventional treatments are treatments involving insertion of a device such as a catheter or a guide wire into a blood vessel in order to remove a stenosis or a thrombus, or to treat cerebral arteriovenous malformation (AVM) by forming a thrombus, for example. Some X-ray diagnostic apparatuses are provided with a road-mapping function, as a function for supporting the procedures of interventional treatments. To support operations of a device inside a blood vessel, the road-mapping function generates a blood vessel image using image data including blood vessel information acquired using a contrast agent, and displays the generated blood vessel image in a manner masking a corresponding fluoroscopic image. For example, by referring to a blood vessel image presented by the road-mapping function, an operator can understand the blood stream, and therefore, the operator can perform the procedures efficiently. Furthermore, by using the road-mapping function, the dose of the contrast agent can be reduced, so that the burden on the subject can be reduced. Hereinafter, the image data including blood vessel information acquired using a contrast agent will be referred to as blood vessel data, and the blood vessel image displayed in a manner superimposed over the fluoroscopic image in a roadmap is referred to as a mask image.

When performed is two-dimensional road-mapping using a mask image generated from two-dimensional blood vessel data, the X-ray diagnostic apparatus can generate the blood vessel data in a short time. The X-ray diagnostic apparatus can therefore update the blood vessel data easily even when the blood stream changes due to the insertion of the device, for example. The two-dimensional road-mapping, however, is not quite capable of clearly displaying a complicated blood stream. Therefore, operators sometimes have difficulty in finding the route to the treatment site, and the efficiency of the procedures may deteriorate.

BRIEF DESCRIPTION OF THE DRAWINGS

FIG. 8 is a flowchart for explaining the sequence of a process performed by the X-ray diagnostic apparatus according to the first embodiment;

FIG. 10 is a flowchart for explaining the sequence of a process performed by an X-ray diagnostic apparatus according to the second embodiment;

DETAILED DESCRIPTION

According to an embodiment, an X-ray diagnostic apparatus comprises processing circuitry. The processing circuitry is configured to acquire a plurality of X-ray images over time based on X-rays having passed through a subject injected with a contrast agent. And the processing circuitry is configured to calculate a blood vessel region corresponding to an inflow path of the contrast agent leading to a predetermined position in a blood vessel region represented in the X-ray images, based on a temporal transition of signal intensities of the contrast agent in the blood vessel region in the X-ray images. And the processing circuitry is configured to perform control to display the blood vessel region corresponding to the inflow path in a display mode that is different from that of a blood vessel region other than the inflow path on a display.

An X-ray diagnostic apparatus according to some embodiments will now be explained with reference to some drawings.

Figure 1:
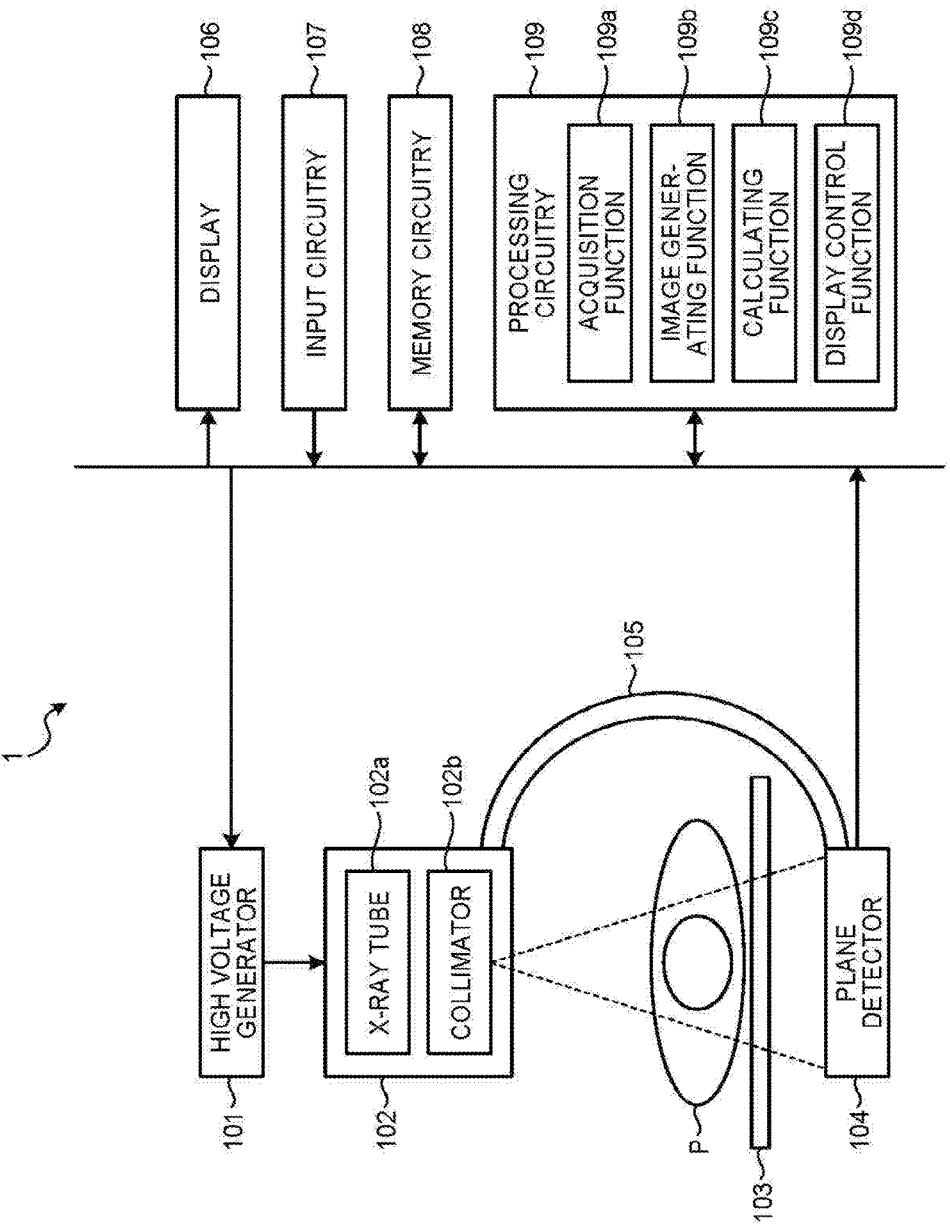
FIG. 1 is a block diagram illustrating an exemplary configuration of an X-ray diagnostic apparatus according to a first embodiment.

An exemplary configuration of an X-ray diagnostic apparatus 1 according to a first embodiment will now be explained with reference to FIG. 1. FIG. 1 is a block diagram illustrating an exemplary configuration of the X-ray diagnostic apparatus 1 according to the first embodiment. As illustrated in FIG. 1, the X-ray diagnostic apparatus 1 according to the first embodiment includes a high voltage generator 101, an X-ray source 102, a tabletop 103, a plane detector 104, a holding arm 105, a display 106, input circuitry 107, memory circuitry 108, and processing circuitry 109.

The high voltage generator 101 generates a high voltage, and supplies the generated high voltage to the X-ray source 102, under the control of the processing circuitry 109. The X-ray source 102 includes an X-ray tube 102a and a collimator 102b. The X-ray tube 102a generates X-rays using the high voltage supplied from the high voltage generator 101. The collimator 102b controls the radiation field of the X-rays in order to reduce the exposure dose on a subject P, and to improve the image quality of the image.

The tabletop 103 is a bed on which the subject P is laid, and is positioned on top of a table not illustrated. The plane detector 104 has a plurality of X-ray detection elements, and detects signal intensity distribution data of the X-rays having passed through the subject P, and transmits the detected distribution data to the processing circuitry 109. The holding arm 105 holds the X-ray source 102 and the plane detector 104 in a manner facing each other with the subject P interposed therebetween.

The display 106 is a monitor referred by the operator, and displays various types of X-ray images, such as an X-ray image acquired using a contrast agent, a fluoroscopic image generated one after another during the procedures, and a mask image displayed in a manner superimposed over the fluoroscopic image, under the control of the processing circuitry 109. The mask image to be displayed will be described later in detail. The input circuitry 107 is provided with a mouse, a keyboard, a trackball, a switch, a button, a joystick, or the like used for entering various types of instructions and settings, and receives instructions and settings from the operator.

The memory circuitry 108 stores therein data used by the processing circuitry 109 that controls the entire processes executed by the X-ray diagnostic apparatus 1. The memory circuitry 108 stores therein, for example, various types of settings used in the processes of acquiring X-ray images, calculating routes, and displaying the routes on the mask image, for example. The memory circuitry 108 also stores therein computer programs executed by the processing circuitry 109. The memory circuitry 108 also stores therein the various types of X-ray images.

The processing circuitry 109 executes a acquisition function 109a, an image generating function 109b, a calculating function 109c, and a display control function 109d. In the embodiment illustrated in FIG. 1, each of the processing functions executed by the acquisition function 109a, the image generating function 109b, the calculating function 109c, and the display control function 109d which are the elements included in the processing circuitry 109 is recorded as a computer program that is executable by a computer in the memory circuitry 108. The processing circuitry 109 is a processor for implementing the function corresponding to a computer program by reading the computer program from the memory circuitry 108, and by executing the computer program. In other words, the processing circuitry 109 having read the computer program has the functions illustrated in the processing circuitry 109 in FIG. 1. In the example illustrated in FIG. 1, the processing functions executed by the acquisition function 109a, the image generating function 109b, the calculating function 109c, and the display control function 109d are implemented using processing circuitry, but it is also possible for the processing circuitry to be configured as a combination of a plurality of independent processors, and for the functions to be implemented by causing the respective processors to execute the respective computer programs.

The term "processor" used in the explanation above means circuitry such as a central processing unit (CPU), a graphics processing unit (GPU), an application specific integrated circuit (ASIC), or a programmable logic device (such as a simple programmable logic device (SPLD), a complex programmable logic device (CPLD), or a field programmable gate array (FPGA)). The processor implements the functions by reading and executing a computer program stored in the memory circuitry 108. The computer program may be directly embedded in circuitry in a processor, instead of storing the computer program in the memory circuitry 108. In such a configuration, the processor implements the functions by reading and executing the computer program embedded in the circuitry. The processors according to the embodiment may also be provided as a combination of a plurality of independent circuits functioning as one processor, and implement the functions thereby, without limitation to a configuration in which each processor is provided as one circuit. Furthermore, a plurality of elements illustrated in FIG. 1 may be integrated into one processor implementing the functions.

The acquisition function 109a according to the first embodiment is an example of a acquisition process performed by processing circuitry as defined in the appended claims. Furthermore, the image generating function 109b according to the first embodiment is an example of an image generating process performed by the processing circuitry as defined in the appended claims. Furthermore, the calculating function 109c according to the first embodiment is an example of a calculating process performed by the processing circuitry as defined in the appended claims. Furthermore, the display control function 109d according to the first embodiment is an example of a display control process performed by the processing circuitry as defined in the appended claims.

The processing circuitry 109 controls the entire process performed by the X-ray diagnostic apparatus 1. The process performed by the X-ray diagnostic apparatus 1 is a sequence of processes related to the road-mapping function such as acquiring X-ray images, calculating a route, and displaying the route on the mask image of the roadmap. The processing circuitry 109 according to the first embodiment acquires a plurality of X-ray images over time, based on the X-rays having passed through the subject F injected with the contrast agent, and calculates a blood vessel region corresponding to an inflow path of the contrast agent leading to a predetermined position in a blood vessel region represented in the acquired X-ray images, based on the temporal transition of the signal intensities of the contrast agent in the blood vessel region in the X-ray images. The processing circuitry 109 displays the blood vessel region corresponding to the inflow path of the contrast agent leading to the predetermined position on the display 106, in a display mode that is different from that of a blood vessel region other than the inflow path, as a route for inserting a device to the predetermined position. These processes performed by the processing circuitry 109 will be described later in detail.

The overall configuration of the X-ray diagnostic apparatus 1 according to the first embodiment is explained above. With such a configuration, the X-ray diagnostic apparatus 1 according to the first embodiment improves the efficiency of the procedures using a blood vessel image by calculating a route to a predetermined position of the blood vessel region, and presenting the calculated route to the operator.

To begin with, a conventional X-ray diagnostic apparatus will be explained. The road-mapping function provided to a conventional X-ray diagnostic apparatus acquires blood vessel data to be used in generating a mask image, two dimensionally or three dimensionally. In the roadmap using three-dimensional blood vessel data, because the blood vessel image is represented three dimensionally, the operator can recognize a blood stream easily. However, it takes time to acquire three-dimensional blood vessel data, and therefore, updating of the blood vessel data is not easy when the shape of the blood vessel changes due to the insertion of a device, for example. The efficiency of the procedures may therefore deteriorate. By contrast, when the conventional X-ray diagnostic apparatus uses two-dimensional blood vessel data in the roadmap, while the updating of the blood vessel data is easy, it is difficult for the operator to recognize the route to the treatment site when the blood stream is complicated, and therefore, the efficiency of the procedures may deteriorate.

To address this issue, the X-ray diagnostic apparatus 1 according to the first embodiment improves the efficiency of the procedures in the two-dimensional road-mapping that uses two-dimensional blood vessel data by calculating the route to the treatment site, and displaying the calculated route. The processes performed by the X-ray diagnostic apparatus 1 according to the first embodiment will now be explained in detail.

The acquisition function 109a acquires X-ray images by controlling an image capturing system that includes the high voltage generator 101, the X-ray source 102, the tabletop 103, the plane detector 104, and the holding arm 105. Specifically, the acquisition function 109a exposes the subject P to X-rays, and detects the X-rays having passed through the subject P using the plane detector 104 by controlling the image capturing system based on various acquisition conditions. The acquisition function 109a then generates image data using electric signals converted from X-rays by the plane detector 104, and stores the generated image data in the memory circuitry 108. For example, the acquisition function 109a generates image data (projection data) by performing a current-to-voltage conversion, an analog-to-digital (A/D) conversion, and a parallel/serial conversion to the electric signals received from the plane detector 104.

The acquisition function 109a generates a piece of image data for each of a captured image and a fluoroscopic image, based on the acquisition conditions. The "fluoroscopic image" herein means an X-ray image generated by causing an X-ray detector to detect the X-rays having passed through the subject P, and displayed in real time as a moving image, for example. The "captured image" also is an X-ray image generated by causing the X-ray detector to detect the X-rays having passed through the subject P, in the same manner as the fluoroscopic image, but with a larger X-ray dose compared with the fluoroscopic image. The X-ray dose is determined based on a recording requirement, for example. To explain using an example, when there is a requirement for recording, a "captured image" with a larger dose is acquired. The "fluoroscopic image" and the "captured image" may be moving images, or still images.

The acquisition function 109a also acquires a plurality of X-ray images based on the X-rays having passed through the subject P injected with the contrast agent. For example, the acquisition function 109a controls the irradiation of X-rays from the X-ray source 102 and the detection of the X-rays by the plane detector 104, while injecting a contrast agent into the blood vessel of the subject P via an injector not illustrated. The acquisition function 109a acquires X-ray images from the subject P with no injection of the contrast agent, and with an injection of the contrast agent. In other words, the acquisition function 109a generates image data captured with no injection of the contrast agent, and the image data captured with an injection of the contrast agent. The acquisition function 109a then stores the generated image data in the memory circuitry 108.

The image generating function 109b applies image processing to the image data stored in the memory circuitry 108, and generates various types of X-ray images. For example, the image generating function 109b generates a captured image and a fluoroscopic image. The image generating function 109b takes a subtraction between the image data acquired while the contrast agent is being injected into the blood vessel, and that acquired without the contrast agent being injected into the blood vessel, and generates a digital subtraction angiography (DSA) image. In other words, the image generating function 109b can generate a blood vessel image in which the contrast agent flowing through a blood vessel region is represented in a more emphasized manner, by subtracting and removing the background such as bones from the blood vessel image in which the contrast agent in the blood vessel is represented using the contrast agent. The image generating function 109b generates a plurality of DSA images over time, by taking subtractions between a plurality of pieces of image data acquired over time with the contrast agent being injected into the blood vessel, and a plurality of respective pieces of image data acquired without the contrast agent being injected. In the explanation below, DSA images are used as an example of X-ray images acquired using a contrast agent.

The image generating function 109b also generates a mask image used in the road-mapping function. The image generating function 109b generates a DSA image as a mask image, for example. The image generating function 109b generates a color image based on the result of the process performed by the calculating function 109c to be described later. Specifically, the image generating function 109b generates a color image each pixel of which is reflected with the color information based on various types of parameters calculated from the temporal transition of the signal intensities, with the parameters calculated for each unit area of the blood vessel region represented in the corresponding DSA image. Such an image representation technique will be hereinafter referred to as parametric imaging. The parameters will be described later in detail. The unit area herein is an area consisting of one pixel in the blood vessel region in the DSA image, or an area consisting of a plurality of pixels (pixel group) in the blood vessel region in the DSA image. Explained below is an example in which the unit area is an area consisting of one pixel. The unit area is hereinafter sometimes simply referred to as a pixel.

The calculating function 109c then calculates an inflow path (hereinafter, referred to as a route) of the contrast agent leading to a predetermined position of the blood vessel region, based on the temporal transition of the signal intensities of the contrast agent in the blood vessel region represented in the DSA images generated by the image generating function 109b. For example, the calculating function 109c calculates a feature quantity (hereinafter, referred to as a parameter) related to a flow of the contrast agent for each pixel, based on the temporal transition of the signal intensity, and calculates the route based on the continuity of the parameter. The route calculation performed by the calculating function 109c according to the first embodiment will now be explained in detail.

Figure 2:
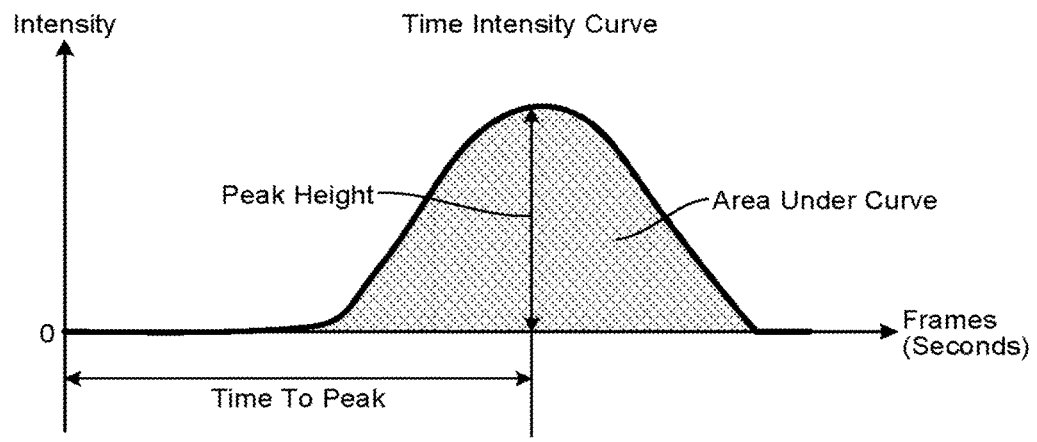
FIG. 2 is a schematic for explaining parameters according to the first embodiment.

To begin with, the calculating function 109c calculates the parameter for each pixel, based on the temporal transition of the signal intensity of the contrast agent in the blood vessel region represented in the DSA images acquired over time. The parameter calculated for each pixel will now be explained with reference to FIG. 2. FIG. 2 is a schematic for explaining the parameters according to the first embodiment. In FIG. 2, the vertical axis represents the signal intensity at each pixel in the blood vessel region in the DSA images, and the horizontal axis represents the number of frames, or the time.

A temporal transition of the signal intensities of the contrast agent is expressed as a time density curve (TDC) illustrated in FIG. 2, for example. As illustrated as the TDC in FIG. 2, denoting the signal intensity at the pixel without any contrast agent as "0", the signal intensity gradually increases as the contrast agent enters the pixel. After the signal intensity reaches its peak, the signal intensity decreases as the contrast agent exits the pixel, and returns to "0". The TDC takes a different shape depending on the pixel.

For example, the calculating function 109c calculates the "time-to-peak (TTP)" representing the time required for the signal intensity to reach its peak, for each pixel in the blood vessel region, as a parameter, based on the temporal transition of the signal intensity of the contrast agent. To explain using an example, the calculating function 109c calculates the time elapsed from when the contrast agent has started being injected into the blood vessel of the subject P until when the signal intensity of the contrast agent reaches its peak, as the TTP. The calculating function 109c may also calculate a "peak height (PH)" representing the peak signal intensity, or an "area under curve (AUC)" representing the cumulative sum of the signal intensities, as a parameter other than the TTP. Furthermore, although illustrated in FIG. 2 are three parameters including TTP, PH, and AUC, the calculating function 109c may also calculate, as parameters not illustrated, "arrival time (AT)" representing the time elapsed until the signal representing the contrast agent appears, a "time to arrival (TTA)" representing the time from when the signal representing the contrast agent has appeared to when the signal intensity exceeds 20 percent of the peak, for example, "wash in" representing the time from when the signal representing the contrast agent has appeared to when the signal intensity reaches its peak, "wash out" representing the time from when the signal intensity reaches its peak to when the contrast agent completely flows out, or "width" indicating the half-width of the peak signal intensity, or "mean transit time (MTT)". Explained below is an example in which the calculating function 109c calculates TTP.

Figure 3:
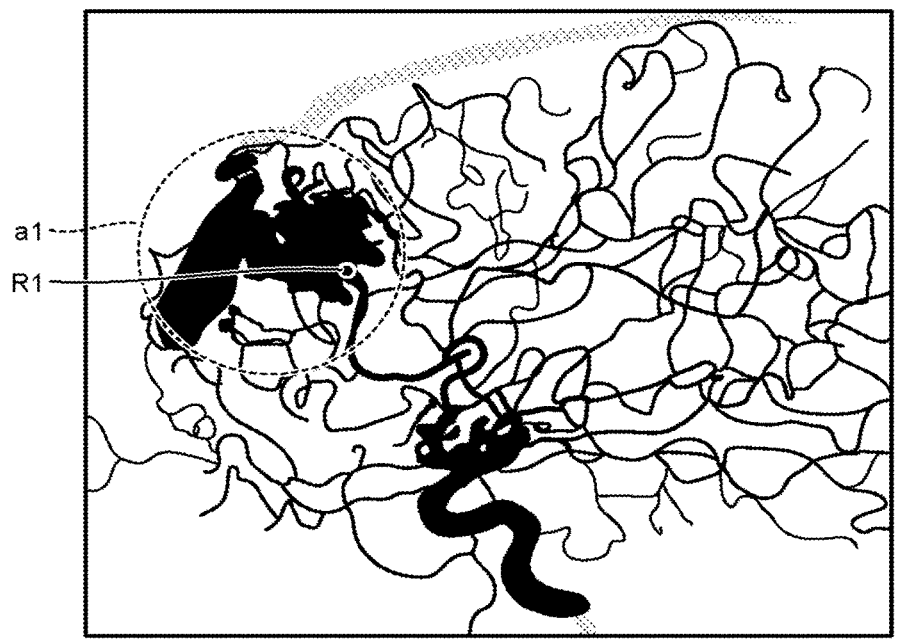
FIG. 3 is a schematic for explaining a predetermined position according to the first embodiment.

The calculating function 109c according to the first embodiment receives the designation of the predetermined position from the operator. FIG. 3 is a schematic for explaining the predetermined position according to the first embodiment. Explained below is an example in which the position R1 illustrated in FIG. 3 is designated as the predetermined position. For example, the display control function 109d presents a DSA image to the operator via the display 106, as illustrated in FIG. 3. The calculating function 109c then receives the designation of the predetermined position in the DSA image, via an operation of a mouse or the like provided to the input circuitry 107. To explain using an example of an AVM case, before performing an interventional treatment to an abnormal tangle of blood vessels (nidus), the operator designates the entry point to a treatment site a1 which is the nidus, as the predetermined position R1, as illustrated in FIG. 3.

Figure 4:
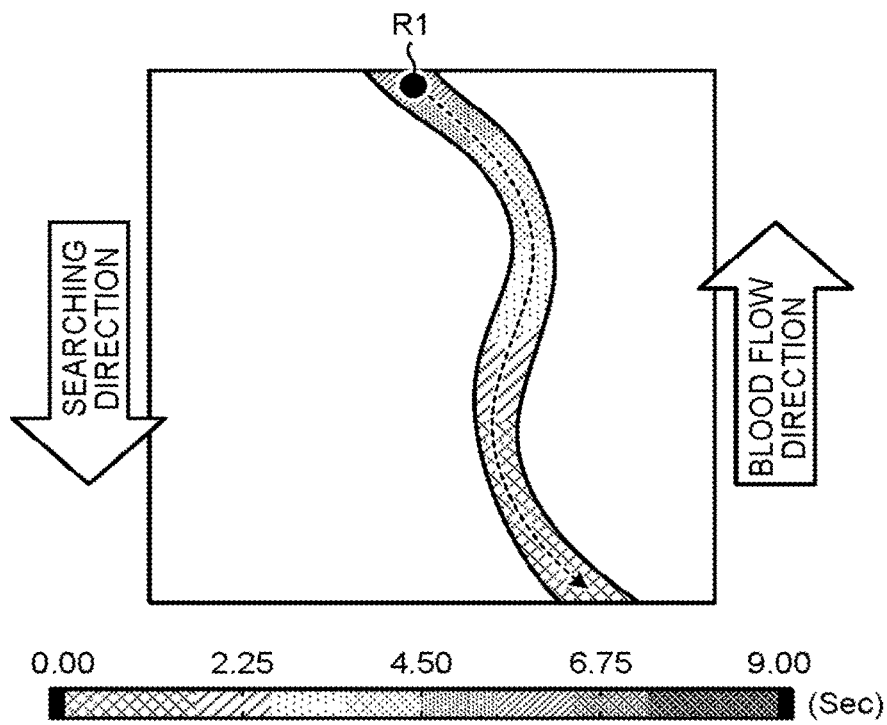
FIG. 4 is a schematic for explaining a route calculation according to the first embodiment.

After the designation of the predetermined position is received, the calculating function 109c calculates a route to the predetermined position R1 based on the continuity of the TTPs calculated for the respective pixels. A route calculation based on the TTP continuity will now be explained with reference to FIG. 4. FIG. 4 is a schematic for explaining the route calculation according to the first embodiment. The top diagram in FIG. 4 represents a color image resultant of coloring a DSA image through TTP-based parametric imaging, and blood flows in a direction from the bottom to the top of the diagram. The bottom diagram in FIG. 4 represents a color bar corresponding to the colors of the color image, and is assigned with colors corresponding to the time (sec) with respect to the time at which the peak signal intensity is reached. Although illustrated in FIG. 4, for the convenience of the explanation, is a color image, the colors are numerically processed internally in the actual process.

As illustrated in FIG. 4, when a blood vessel region is continuous, the TTP exhibits continuous values. The TTP value gradually increases on the downstream side of the blood flow (toward the top of the top diagram in FIG. 4) because the contrast agent flows in the same direction as the blood flow. The calculating function 109c, therefore, calculates a blood vessel region that is continuous to the predetermined position R1, using the continuity of the TTP value.

Specifically, the calculating function 109c calculates a route by sequentially comparing the TTPs at adjacent pixels, starting from the pixel corresponding to the predetermined position R1 as a starting point, in a manner following the TTPs at the respective pixels in the blood vessel region, retrospectively. More specifically, to begin with, the calculating function 109c searches for a pixel with TTP similar to that of the pixel corresponding to the predetermined position R1, or a pixel with a shorter TTP value, from the pixels that are adjacent to the pixel corresponding to the predetermined position R1, and identifies the pixel as a route. The calculating function 109c then calculates a route by repeating this process to the pixels that are adjacent to the pixel identified as a route. For example, the calculating function 109c keeps searching for the route from the predetermined position R1, until the route reaches an edge of the X-ray image, as illustrated in the top diagram in FIG. 4.

An ending point of the route search executed by the calculating function 109c may be at where the route calculation reaches an edge of the X-ray image, as mentioned above, or may be at where the route calculation reaches the tip of the device for injecting the contrast agent. The calculating function 109c may also receive a designation of the ending point of the route search, in addition to the designation of the predetermined position.

Figure 5:
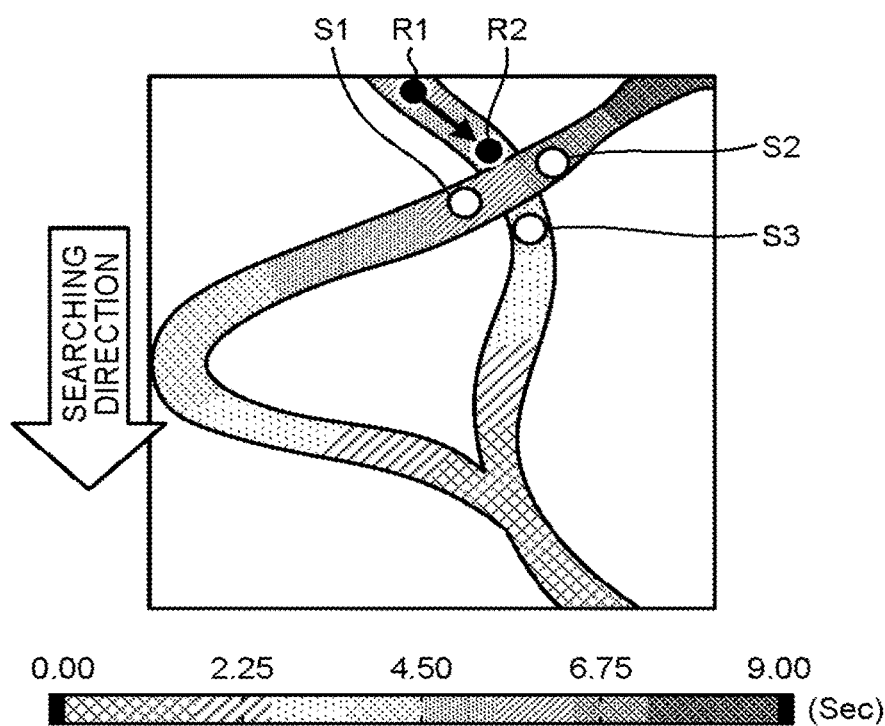
FIG. 5 is a schematic for explaining the route calculation in an intersecting portion in the first embodiment.

A route calculation in an intersecting portion in the blood vessel region will now be explained with reference to FIG. 5. FIG. 5 is a schematic for explaining a route calculation in an intersecting portion according to the first embodiment. Illustrated in FIG. 5, for the convenience of the explanation, is a color image, in the same manner as in FIG. 4, but the colors are numerically processed internally in the actual process. As described earlier, the calculating function 109c calculates a continuous blood vessel region, using the continuity of the TTP value. When the blood vessels are intersecting in the depth direction, for example, as illustrated in FIG. 5, the TTP will not exhibit continuity. For this reason, when the TTPs of adjacent pixels do not exhibit continuity, the calculating function 109c determines the position at which the TTP is not continuous as an intersecting portion, and performs the following process. For example, if the difference between the TTP values at adjacent pixels exceeds a predetermined threshold, the calculating function 109c determines that the TTP values are not continuous. The predetermined threshold may be set to any level. The intersecting portion herein means a portion in which blood vessels not actually intersecting with each other are projected as intersecting with each other in the X-ray image having been acquired two dimensionally. Because the TTP values will exhibit continuity in a portion where the blood vessels are actually intersecting with each other, the calculating function 109c can calculate a route in a manner retrospectively following the TTPs at the respective pixels.

For example, as illustrated in FIG. 5, when the blood vessel region has an intersecting portion in which blood vessels intersect with each other, the calculating function 109c calculates, to begin with, a route from the predetermined position R1 to a position R2 positioned immediately previous to the intersecting portion, following the process described above. At this time, the calculating function 109c determines that there is an intersecting portion based on the discontinuity of the TTP. The calculating function 109c then performs the following process using the positions that are adjacent to the intersecting portion, as route candidates. For example, the calculating function 109c calculates a route through the intersecting portion by establishing three routes including a route including a position S1, a route including a position S2, and a route including a position S3, as candidates of a route subsequent to the position R2 positioned immediately previous to the intersecting portion, and selecting the appropriate one of these three.

Specifically, the calculating function 109c calculates an evaluation, for each of the pixels near the intersecting portion, based on the continuity of the TTPs between that pixel and the pixel at the position R2 immediately previous to the intersecting portion, and based on a positional relation between that pixel and the pixel at the position R2 immediately previous to the intersecting portion, and calculates a route through the intersecting portion based on the calculated evaluation. For example, the calculating function 109c estimates the TTP at each of the pixels at the positions S1 to S3 based on the amount of change in the TTP value between the predetermined position R1 and the position R2 immediately previous to the intersecting portion, and the distance of that pixel with respect to the position R2 immediately previous to the intersecting portion. To explain using an example, the calculating function 109c estimates the TTP at each of the pixels at the positions S1 to S3 by calculating the amount of change in the TTP value resultant of a movement by a distance corresponding to one pixel, as a change ratio, based on the TTP values at the pixels from the predetermined position R1 to the position R2 immediately previous to the intersecting portion, and by multiplying the calculated change ratio to the distance from the position R2 immediately previous to the intersecting portion to each of the pixels at the respective positions S1 to S3. The calculating function 109c then calculates a ratio of the actual TTP at each of the pixels at the positions S1 to S3 with respect to the corresponding TTP estimation, as an evaluation, and identifies the route including the position with a ratio nearest to "1" as the route through the intersecting portion.

The calculating function 109c may also consider the direction of the calculated route from the predetermined position R1 to the position R2 immediately previous to the intersecting portion, in calculating the evaluation used in determining the route through the intersecting portion. To explain using an example, the calculating function 109c establishes, to begin with, the straight line connecting the predetermined position R1 and the position R2 immediately previous to the intersecting portion illustrated in FIG. 5, as an axis. The calculating function 109c then estimates the angle of the route subsequent to the position R2 with respect to the above-mentioned axis, based on the curvature of the route from the predetermined position R1 to the position R2 immediately previous to the intersecting portion. The calculating function 109c calculates a ratio between the estimated angle and the angle formed by the route corresponding to each of the pixels at the positions S1 to S3 and the axis, as an evaluation, and identifies the route including the position resulting in a ratio that is nearest to "1" as the route through the intersecting portion.

The calculating function 109c may calculate another evaluation based on the evaluation related to TTP and the evaluation related to angle. For example, the calculating function 109c may square the difference between the TTP ratio, having been calculated as an evaluation, and "1", and the difference between the angle ratio, having also been calculated as an evaluation, and "1", and calculate the sum of the squares as an evaluation of the route corresponding to each of the positions S1 to S3, and identify the route whose calculated evaluation is the smallest as the route through the intersecting portion.

Once the route through the intersecting portion is identified, the calculating function 109c continues searching for the route subsequent to the intersecting portion, and completes the route calculation. For example, the calculating function 109c calculates the position S3 as the route through the intersecting portion based on the evaluation. The calculating function 109c then searches for a route subsequent to the position S3, and calculates a route from the predetermined position R1 to an edge of the X-ray image.

Figure 6A:
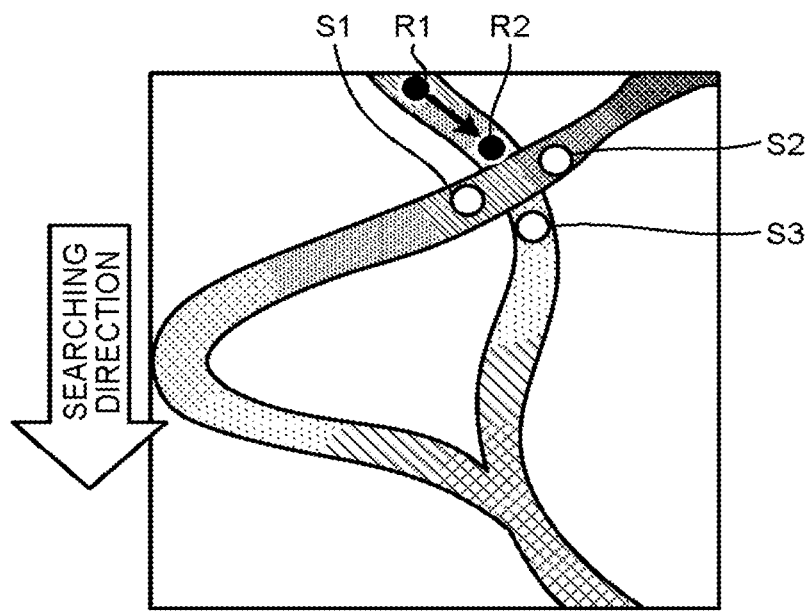
FIG. 6A is a schematic illustrating an exemplary way in which a route is displayed in the first embodiment.
Figure 6B:
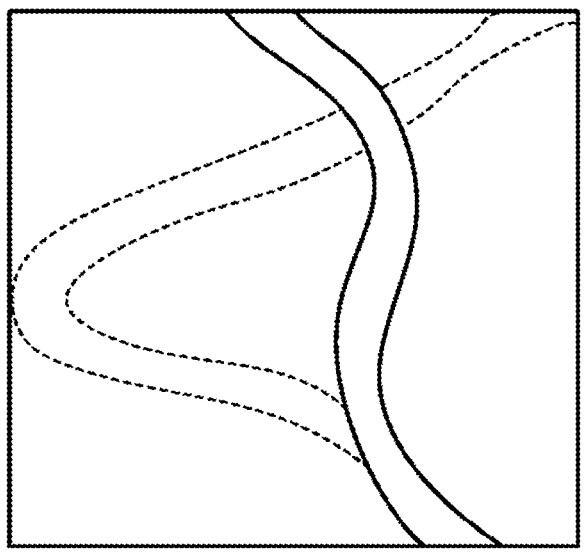
FIG. 6B is a schematic illustrating an exemplary way in which the route is displayed in the first embodiment.

Once the calculating function 109c calculates a route to the predetermined position R1 in the manner described above, the display control function 109d according to the first embodiment displays the calculated route in a display mode that is different from the blood vessel region other than the calculated route, on the display 106. For example, assuming that the calculating function 109c performs a route calculation in the X-ray image illustrated in FIG. 6A, the image generating function 109b generates an image processed in such a manner that the color of the blood vessel region other than the calculated route is transparent, and only the calculated route is visible, as illustrated in FIG. 6B. FIGS. 6A and 6B are schematics illustrating an exemplary way in which the route is displayed in the first embodiment. The processed image illustrated in FIG. 6B is resultant of determining the route including the position S3 as the route through the intersecting portion, in the X-ray image illustrated in FIG. 6A.

Figure 7A:
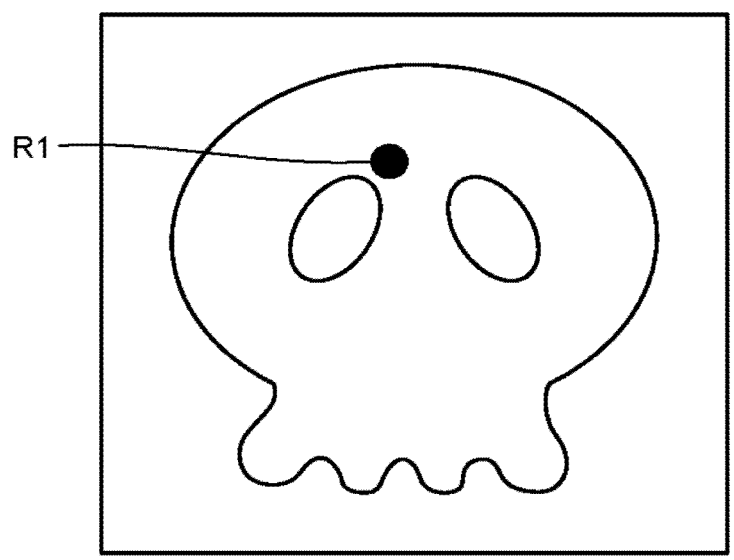
FIG. 7A is a schematic illustrating an exemplary way in which the route is displayed in the first embodiment.
Figure 7B:
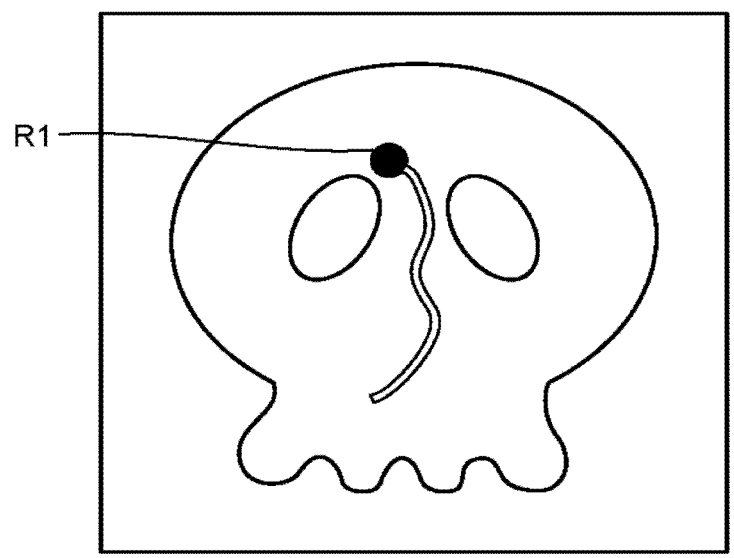
FIG. 7B is a schematic illustrating an exemplary way in which the route is displayed in the first embodiment.

The display control function 109d also displays the processed image generated by the image generating function 109b, as a mask image for the roadmap, on the display 106. For example, the display control function 109d displays the route to the predetermined position R1 calculated by the calculating function 109c, as a mask image for the roadmap, as illustrated in FIG. 7B, by displaying the processed image illustrated in FIG. 6B in a manner superimposed over the fluoroscopic image illustrated in FIG. 7A. FIGS. 7A and 7B are schematics illustrating an exemplary way in which the route is displayed in the first embodiment.

When the shape of the blood vessel changes as the device is operated in the blood vessel, or when there is a possibility for the shape of the blood vessel having been changed, for example, the operator can update the mask image for the roadmap. Specifically, when the X-ray diagnostic apparatus 1 according to the first embodiment receives a mask image updating instruction from the operator, the X-ray diagnostic apparatus 1 acquires the DSA images again, generates a mask image from the acquired DSA images through the process described above, and presents the latest mask image to the operator.

The sequence of an exemplary process performed by the X-ray diagnostic apparatus 1 will now be explained with reference to FIG. 8. FIG. 8 is a flowchart for explaining the sequence of a process performed by the X-ray diagnostic apparatus 1 according to the first embodiment. Steps S102 and S110 are steps corresponding to the image generating function 109b. Steps S103, S104, S105, S106, S107, S108, and S109 are steps corresponding to the calculating function 109c. Step S111 is a step corresponding to the display control function 109d.

To begin with, the processing circuitry 109 acquires various types of settings related to an execution of the road-mapping function from the memory circuitry 108 (Step S101), and generates a plurality of DSA images over time (Step S102). The processing circuitry 109 then calculates the TTP for each pixel, based on the temporal transition of the signal intensities in the blood vessel region represented in the DSA images (Step S103). The processing circuitry 109 then acquires the predetermined position in the blood vessel region (Step S104), and searches for a route from the predetermined position, based on the continuity of the TTP (Step S105).

The processing circuitry 109 then determines whether there is an intersecting portion in the blood vessel region (Step S106). If there is an intersecting portion in the direction of the route search (Yes at Step S106), the processing circuitry 109 calculates an evaluation for each pixel near the intersecting portion (Step S107), determines the route through the intersecting portion based on the calculated evaluations (Step S108), and shifts the process back to Step S105. If there is no intersecting portion (No at Step S106), the processing circuitry 109 determines whether the route calculation has been completed (Step S109). If the route calculation has not been completed yet (No at Step S109), the processing circuitry 109 shifts the process back to Step S105. If the route calculation has been completed (Yes at Step S109), the processing circuitry 109 generates a mask image (Step S110), and displays a roadmap over the fluoroscopic image (Step S111). The processing circuitry 109 then determines whether an instruction for repeating the generation of DSA images has been received (Step S112). If an instruction for repeating the generation of DSA images has been received (Yes at Step S112), the processing circuitry 109 shifts the process back to Step S102. If any instruction for repeating the generation of DSA images has not been received (No at Step S112), the processing circuitry 109 determines whether an ending command has been received (Step S113). If the ending command has not been received (No at Step S113), the X-ray diagnostic apparatus 1 transits to a standby mode. If the ending command has been received (Yes at Step S113), the process is ended.

As described above, according to the first embodiment, the acquisition function 109a acquires a plurality of X-ray images over time, based on the X-rays having passed through the subject P injected with the contrast agent. Furthermore, the calculating function 109c calculates a blood vessel region corresponding to the inflow path of the contrast agent leading to the predetermined position in the blood vessel region represented in the X-ray images, based on the temporal transition of the signal intensities of the contrast agent in the blood vessel region in the X-ray images. The display control function 109d then displays the blood vessel region corresponding to the inflow path calculated by the calculating function 109c in a display mode that is different from that of a blood vessel region other than the inflow path on the display 106. By calculating the route to the treatment site, and displaying the calculated route in the mask image for the roadmap, the X-ray diagnostic apparatus 1 according to the first embodiment can improve the efficiency of the procedures even when the blood stream is complicated.

Furthermore, according to the first embodiment, because the road-mapping is performed using two-dimensional blood vessel data, the blood vessel data can be updated easily, even when the shape of the blood vessel changes due to the insertion of a device, for example. By presenting a roadmap updated as required to the operator, the X-ray diagnostic apparatus 1 according to the first embodiment can improve the efficiency of the procedure.

Furthermore, according to the first embodiment, even when the blood vessel region has an intersecting portion in which blood vessels intersect with each other, the calculating function 109c calculates an evaluation, for each pixel near the intersecting portion, based on the continuity between the parameters at that pixel and the pixel immediately previous to the intersecting portion, and a positional relation between that pixel and the pixel immediately previous to the intersecting portion in the blood vessel region, and calculates the route through the intersecting portion based on the calculated evaluations. Therefore, the X-ray diagnostic apparatus 1 according to the first embodiment can calculate an accurate route through an intersecting portion of the blood vessel region.

Furthermore, according to the first embodiment, when there is an intersecting portion, the calculating function 109c calculates an evaluation, for each pixel near the intersecting portion, the continuity between the parameters at that pixel and the pixel immediately previous to the intersecting portion, a positional relation between that pixel and the pixel immediately previous to the intersecting portion in the blood vessel region, and the direction of the route to the pixel immediately previous to the intersecting portion, and then calculates the route through the intersecting portion based on the calculated evaluations. Therefore, the X-ray diagnostic apparatus 1 according to the first embodiment can calculates a route more accurately in an intersecting portion of the blood vessel region.

Furthermore, the X-ray diagnostic apparatus 1 according to the first embodiment performs control to display only the calculated route in the mask image for the roadmap. By displaying the route to the treatment site in an easy-to-understand manner, without displaying the blood vessel image other than the target route, the X-ray diagnostic apparatus 1 according to the first embodiment can improve the efficiency of the procedure, even when the blood stream is complicated.

Explained in the first embodiment is an example in which one parameter is calculated, and the route is calculated based on the calculated parameter. By contrast, in a second embodiment, a plurality of parameters are calculated for an intersecting portion of the blood vessel region, and the route is calculated based on the calculated parameters.

The X-ray image diagnostic apparatus according to the second embodiment has a configuration that is the same as that of the X-ray image diagnostic apparatus according to the first embodiment illustrated in FIG. 1, but the process performed by the calculating function 109c is partly different. Therefore, the configurations that are the same as those explained in the first embodiment are the same reference numerals as those in FIG. 1, and redundant explanations thereof will be omitted.

Figure 9:
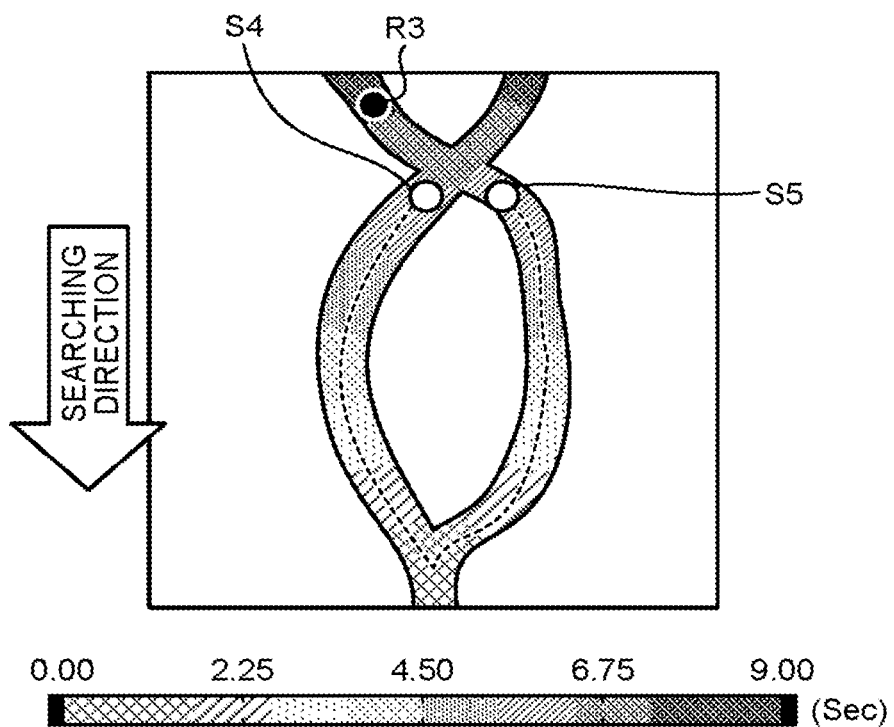
FIG. 9 is a schematic for explaining a route calculation in an intersecting portion in a second embodiment.

A route calculation in an intersecting portion according to the second embodiment will now be explained with reference to FIG. 9. FIG. 9 is a schematic for explaining a route calculation in an intersecting portion in the second embodiment. The top diagram in FIG. 9 represents a color image resultant of coloring a DSA image through TTP-based parametric imaging, and blood flows in the direction from the bottom to the top of the diagram. The bottom diagram in FIG. 9 represents a color bar corresponding to the colors of the color image, and is assigned with colors corresponding to the time (sec) with respect to the time at which the peak signal intensity is reached. Although illustrated in FIG. 9 for the convenience of the explanation is a color image, the colors are numerically processed internally, in the actual process.

For example, as illustrated by the color image in FIG. 9, if there is an intersecting portion in the route search from a predetermined position R3, the calculating function 109c determines one of a route including a position S4 and a route including a position S5 as the route. If the pixels at the respective position S4 and position S5 that are immediately following the intersecting portion have similar TTPs, as illustrated in FIG. 9, these routes may have evaluations that are not be very different, and the reliability of the route determination may be insufficient.

To explain using an example, the calculating function 109c estimates the TTP at each of the pixels at the position S4 and the position S5, based on the amount of change in the TTP from the predetermined position R3 to the position immediately previous to the intersecting portion, and based on the distance between such a pixel and the position immediately previous to the intersecting portion. The calculating function 109c then calculates a ratio of the actual TTP at each of the pixels at the positions S4 and S5 with respect to the TTP estimation, as an evaluation. If the difference between the ratios calculated as the evaluations of the respective routes is equal to or less than "0.1", for example, the calculating function 109c determines that reliability of the route determination is not sufficient.

To address this issue, the calculating function 109c according to the second embodiment calculates an additional parameter, PH or AUC, for example, for each of the pixels near the intersecting portion, in order to improve the reliability of the route determination. Explained below is an example in which the calculating function 109c calculates the PH, which is the peak signal intensity, as the additional parameter. The calculating function 109c calculates PH for each of the pixels near the intersecting portion, and calculates a PH-related evaluation, for each of such pixels, based on the continuity of the PH at such a pixel and the PH at the pixel immediately previous to the intersecting portion, and based on a positional relation between such a pixel and the pixel immediately previous to the intersecting portion in the blood vessel region.

When calculated for each of the pixels near the intersecting portion, in addition to the TTP-related evaluation, is the PH-related evaluation, the calculating function 109c according to the second embodiment can calculate a route through the intersecting portion based on the PH-related evaluations, as long as the PH-related evaluations among such routes are different, even when the TTP-related evaluations among such routes may not be very different. Even with the PH-related evaluations calculated, the reliability of the route determination may still be low. In such a case, the calculating function 109c can additionally calculate another parameter.

In a configuration in which a plurality of parameters are calculated, the calculating function 109c may calculate one evaluation for each of these parameters, or calculate one integral evaluation for all of the parameters. Furthermore, AUC or MTT, without limitation to PH, may be calculated as the additional parameter, or a plurality of additional parameters may be calculated, when the route determination is not sufficiently reliable. Furthermore, a plurality of parameters may be calculated in advance, instead of calculating the additional parameter under the condition of the route determination being not sufficiently reliable.

The sequence of an exemplary process performed by the X-ray diagnostic apparatus 1 will now be explained with reference to FIG. 10. FIG. 10 is a flowchart for explaining the sequence of a process performed by the X-ray diagnostic apparatus 1 according to the second embodiment. Steps S202 and S211 are steps corresponding to the image generating function 109b. Steps S203, S204, S205, S206, S207, S208, S209, and S210 are steps corresponding to the calculating function 109c. Step S212 is a step corresponding to the display control function 109d.

To begin with, the processing circuitry 109 acquires various types of settings related to an execution of the road-mapping function from the memory circuitry 108 (Step S201), and generates a plurality of DSA images over time (Step S202). The processing circuitry 109 then calculates the TTP for each of the pixels, based on the temporal transition of the signal intensities in the blood vessel region in the DSA images (Step S203). The processing circuitry 109 then acquires the predetermined position in the blood vessel region (Step S204), and searches for a route from the predetermined position, based on the continuity of the TTP (Step S205).

The processing circuitry 109 then determines whether there is an intersecting portion in the blood vessel region (Step S206). If there is an intersecting portion in the direction of the route search (Yes at Step S206), the processing circuitry 109 calculates an evaluation for each pixel near the intersecting portion (Step S207), and determines a route through the intersecting portion based on the calculated evaluations (Step S208). If the route is determined (Yes at Step S208), the processing circuitry 109 shifts the process back to Step S205. If the route through the intersecting portion is not determined (No at Step S208), the processing circuitry 109 calculates an additional parameter for each of the pixels near the intersecting portion (Step S209), shifts the process back to Step S207, and calculates an evaluation for the additional parameter.

If there is no intersecting portion (No at Step S206), the processing circuitry 109 determines whether the route calculation has been completed (Step S210). If the route calculation has not been completed yet (No at Step S210), the processing circuitry 109 shifts the process back to Step S205. If the route calculation has been completed (Yes at Step S210), the processing circuitry 109 generates a mask image (Step S211), and displays a roadmap on the fluoroscopic image (Step S212). The processing circuitry 109 then determines whether an instruction for repeating the generation of DSA images has been received (Step S213). If an instruction for repeating the generation of DSA images has been received (Yes at Step S213), the processing circuitry 109 shifts the process back to Step S202. If any instruction for repeating the generation of DSA images has not been received (No at Step S213), the processing circuitry 109 determines whether an ending command has been received (Step 3214). If the ending command has not been received (No at Step S214), the X-ray diagnostic apparatus 1 transits to a standby mode. If the ending command has been received (Yes at Step S214), the process is ended.

The processing circuitry 109 may use various techniques, without limitation to the technique calculating the additional parameter, to calculate the route, when the route is not determined at Step S208. For example, the processing circuitry 109 may calculate the route through the intersecting portion in the DSA images by acquiring the DSA images from a plurality of directions, and comparing the TTPs and the spatial coordinates among the DSA images acquired from the respective directions.

The processing circuitry 109 may also calculate a plurality of routes when the route is not determined at Step S208. To explain using an example, the processing circuitry 109 may calculate a difference between the evaluations of the respective routes, and if the difference in the evaluation among the route does not exceed a predetermined threshold, the processing circuitry 109 may calculate a plurality of routes. The processing circuitry 109 may also be configured to receive an operation for selecting one of a plurality of calculated routes.

As described above, the calculating function 109c according to the second embodiment calculates a plurality of parameters, calculates evaluations based on the calculated parameters, and calculates the route through the intersecting portion based on the calculated evaluations. Therefore, the X-ray diagnostic apparatus 1 according to the second embodiment can calculate a more reliable route through the intersecting portion, and improve the efficiency of the procedures by presenting the more accurate route to the operator.

Furthermore, as described above, when the reliability of the route determination based on the evaluations is insufficient, the calculating function 109c according to the second embodiment calculates a plurality of routes through the intersecting portion. Therefore, the X-ray diagnostic apparatus 1 according to the second embodiment can avoid an inaccurate route from being presented.

In the first embodiment, the example illustrated in FIGS. 7A and 7B is explained an exemplary way in which the calculated route is displayed. In a third embodiment, by contrast, a variation of the exemplary way of the calculated route will be explained.

The X-ray image diagnostic apparatus according to the third embodiment has a configuration that is the same as that of the X-ray image diagnostic apparatus according to the first embodiment illustrated in FIG. 1, but the processes performed by the image generating function 109b and the display control function 109d are partly different. Therefore, the configurations that are the same as those explained in the first embodiment are the same reference numerals as those in FIG. 1, and redundant explanations thereof will be omitted.

Figure 11A:
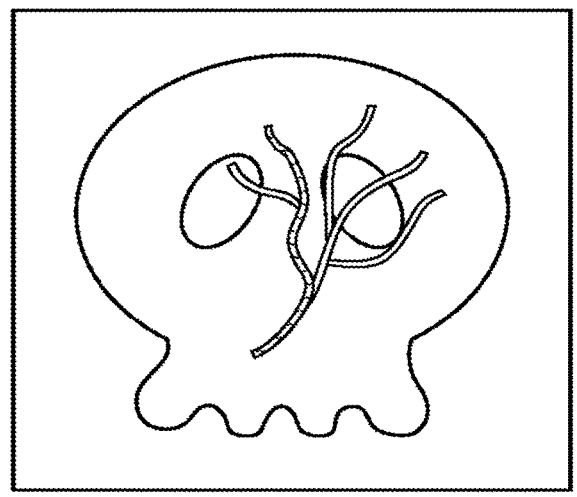
FIG. 11A is a schematic illustrating an exemplary way in which a route is displayed in a third embodiment.
Figure 11B:
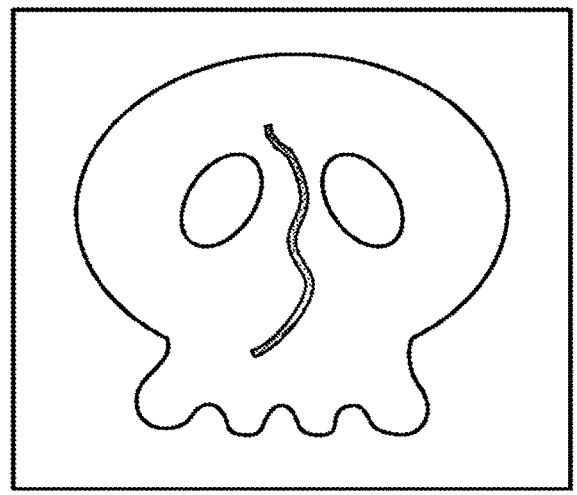
FIG. 11B is a schematic illustrating an exemplary way in which the route is displayed in the third embodiment.
Figure 11C:
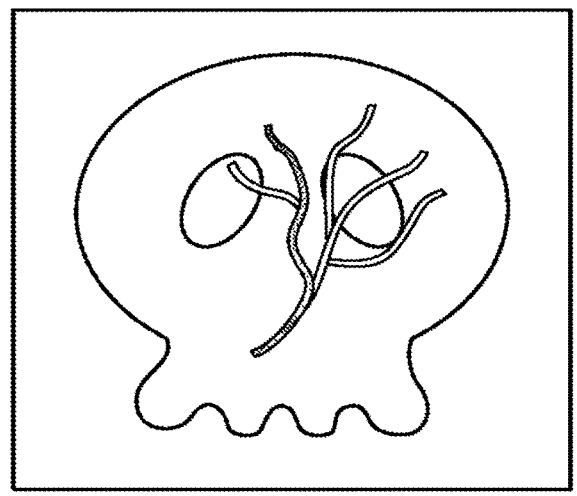
FIG. 11C is a schematic illustrating an exemplary way in which the route is displayed in the third embodiment.

An exemplary way in which the route is displayed in the third embodiment will now be explained with reference to FIGS. 11A to 11C. FIGS. 11A to 11C are schematics illustrating an exemplary way in which a route is displayed in the third embodiment. For example, the image generating function 109b according to the third embodiment generates a mask image in which the blood vessel region corresponding to the route calculated by the calculating function 109c is emphasized in the blood vessel region represented in the DSA image. At this time, as an example, the image generating function 109b emphasizes the route by representing the blood vessel region calculated as a route in a color or shade that is different from that in which the other blood vessel region is represented. The display control function 109d according to the third embodiment then displays the mask image generated by the image generating function 109b in the roadmap, as illustrated in FIG. 11A.

The display control function 109d according to the third embodiment can use a color image resultant of the parametric imaging as a mask image of the roadmap. For example, the image generating function 109b generates a color image each pixel of which has a color determined based on the TTP, and generates a mask image for displaying only the blood vessel region corresponding to the calculated route in the blood vessel region represented in the color image. The display control function 109d then displays the mask image generated by the image generating function 109b in a manner superimposed over the fluoroscopic image, on the display 106, as illustrated in FIG. 11B.

For example, the image generating function 109b may also generate a mask image by superimposing the blood vessel region corresponding to the calculated route in the blood vessel region represented in the color image generated by the parametric imaging, over the blood vessel region represented in the DSA image, and the display control function 109d may display the mask image generated by the image generating function 109b by superimposing the mask image over the fluoroscopic image on the display 106, as illustrated in FIG. 11C.

As described above, the display control function 109d displays the blood vessel region corresponding to the calculated route and the blood vessel region other than the calculated route in different display modes on the display 106. The different display modes may be any display modes enabling the operator to distinguish the blood vessel region corresponding to the calculated route from the blood vessel region other than the calculated route. For example, the display control function 109d may use different hue, brightness, saturation, or the like for the blood vessel region corresponding to the calculated route and the blood vessel region other than the calculated route, or display the blood vessel region other than the calculated route transparently or opaquely. The display control function 109d may also display the blood vessel region corresponding to the calculated route transparently or opaquely. As other examples, the display control function 109d may display one of the blood vessel region corresponding to the calculated route and the blood vessel region other than the calculated route blinkingly, or display an arrow or a line along the blood vessel region corresponding to the calculated route.

With the exemplary way of displaying described above, the X-ray diagnostic apparatus 1 according to the third embodiment can reduce the burden of the operator in understanding the route to the treatment site, and improve the efficiency of the procedures. Furthermore, by displaying the route to the treatment site using the color image resultant of parametric imaging, depth-direction information can be acquired in a two-dimensional roadmap. For example, when the mask image has any section in which the change in the color is gradual in the blood vessel region presented in colors, it can be assumed that the blood vessel is running in parallel with the mask image in such a section. When the mask image has any section in which the colors changes steeply, it can be assumed that the blood vessel is running in perpendicularly to the mask image in such a section. In this manner, the X-ray diagnostic apparatus 1 according to the third embodiment can present the depth-direction information to the operator even in a two-dimensional roadmap, and therefore, the efficiency of the procedure can be improved further.

Explained in the first to the third embodiments is an example in which, when the blood vessel region has an intersecting portion in which blood vessels intersect with each other, the calculating function 109c calculates, for each pixel near the intersecting portion, an evaluation that is based on the continuity of a parameter at such a pixel and the parameter at the pixel immediately previous to the intersecting portion, and based on a positional relation between such a pixel and the pixel immediately previous to the intersecting portion in the blood vessel region, and calculates a route through the intersecting portion based on the calculated evaluations. The embodiment is, however, not limited to such an example.

For example, when the blood vessel region has an intersecting portion in which blood vessels intersect with each other, the calculating function 109c may calculate, for each pixel near the intersecting portion, a vector (optical flow) representing a movement of the contrast agent, and calculate a route through the intersecting portion based on the similarity of the vectors in the respective pixels. To explain using an example, to begin with, the calculating function 109c calculates a vector representing a movement of the contrast agent by connecting the position of the contrast agent in one time frame and the position of the contrast agent in the subsequent time frame, in the DSA images acquired over time.

The calculating function 109c then calculates a difference in the magnitude and the direction (angle) between the vectors in the respective pixels near the intersecting portion. For example, the calculating function 109c calculates these differences in the pixel immediately previous to the intersecting portion, and the pixel positioned adjacently in the searching direction (in the opposite direction of the blood flow). The calculating function 109c then sequentially calculates the differences to the pixels adjacently positioned in the searching direction, using the pixel immediately previous to the intersecting portion as a starting point, for each of the pixels positioned near the intersecting portion.

The calculating function 109c then compares the calculated differences with respective thresholds set for the magnitude and the direction (angle) of such a vector. The calculating function 109c then determines whether each of the pixels is a pixel included in the route, based on whether each of the calculated differences is equal to or less than a corresponding threshold, and calculates a route through the intersecting portion. For example, even when some pixel has TTP that is similar to that at the pixel immediately previous to the intersecting portion, the calculating function 109c determines the pixel as not included in the route if the calculated differences exceed the respective thresholds, and the magnitudes and the directions (angles) of the vectors are very different. As another example, the calculating function 109c determines a pixel to be included in the route if the calculated differences are smaller than the respective thresholds, and the magnitudes and the directions (angles) of the vectors are similar, between the pixels with TTP similar to that at the pixel immediately previous to the intersecting portion.

As another example, when the blood vessel region has an intersecting portion in which blood vessels intersect with each other, the calculating function 109c calculates the route through the intersecting portion by performing computational fluid dynamics (CFD) based on the DSA images. To explain using an example, to begin with, the calculating function 109c calculates the conditions of the blood flow (such as the speed, the direction, the flow rate, and the pressure of the blood flow) at each position of the blood vessel region in the DSA images using CFD, based on the positions of the contrast agent represented in the DSA images.

In the intersecting portion, there is a blood vessel through which the blood flows into the intersecting portion, and another blood vessel through which the blood flows out of the intersecting portion. For example, when the intersecting portion has a cross-like shape, four blood vessels extend from the intersecting portion, and at least one of the four blood vessels is a blood vessel through which the blood flows into the intersecting portion, and at least one of the four is a blood vessel through which the blood flows out of the intersecting portion. The pixel immediately previous to the intersecting portion in a route search is included in the blood vessel through which the blood flows out of the intersecting portion.

When there is one blood vessel through which the blood flows into the intersecting portion, and there are three blood vessels through which the blood flows out of the intersecting portion, the calculating function 109c determines that this intersecting portion is a point where the blood vessel branches out, and these blood vessels are actually connected. The calculating function 109c also determines that the only blood vessel through which the blood flows into the intersecting portion as the route.

By contrast, when there are two blood vessels through which the blood flows into the intersecting portion, and there are two blood vessels through which the blood flows out of the intersecting portion, the calculating function 109c determines that blood vessels are not actually connected, but simply are represented as overlapping each other. The calculating function 109c also compares the conditions of the blood flow in one of the two blood vessels through which the blood flows out of the intersecting portion and that includes the pixel immediately previous to the intersecting portion, with the conditions of the blood flow in each of the two blood vessels through which the blood flows into the intersecting portion. The calculating function 109c then identifies the blood vessel with the blood flow conditions that are similar to those of the blood vessel including the pixel immediately previous to the intersecting portion (with matching flow rates, for example), as the route, among the two blood vessels through which the blood flows into the intersecting portion.

As another example, when the blood vessel region has an intersecting portion in which blood vessels intersect with each other, the calculating function 109c calculates a route through the intersecting portion, based on the similarity in the temporal transitions of the signal intensities of the contrast agent at these pixels. To explain using an example, the calculating function 109c calculates, for each pixel near the intersecting portion, a TDC representing the temporal transition of the signal intensities of the contrast agent. Furthermore, the calculating function 109c calculates, for each of the pixels near the intersecting portion, a value representing a position of the TDC (such as the time at which the signal representing the contrast agent appears, the time at which the signal representing the contrast agent reaches its peak, or the time at which the signal representing the contrast agent disappears), the TDC height (the peak of the signal representing the contrast agent, the integration of the signal representing the contrast agent), the shape of the TDC (such as the intensity of the signal representing the contrast agent at any point in time from when the signal representing the contrast agent has appeared to when the signal disappears, and an inclination of the graph), for example.

The calculating function 109c then calculates a difference between the TDC-related values calculated for the respective pixels near the intersecting portion. For example, the calculating function 109c calculates such a difference in the pixel immediately previous to the intersecting portion and the pixel positioned adjacently to such a pixel in the searching direction. The calculating function 109c then sequentially calculates the difference for each of the pixels near the intersecting portion, with respect to the pixel that is adjacently positioned in the searching direction position, using the pixel immediately previous to the intersecting portion as a starting point.

The calculating function 109c then calculates the route through the intersecting portion by comparing the calculated difference with a predetermined threshold, and determining whether the pixel is a pixel to be included in the route based on whether the calculated difference is equal to or less than the threshold. For example, if the calculated difference is greater than the threshold, and the pixel has a very different TDC, the calculating function 109c determines the pixel as not to be included in the route even if the TTP at the pixel is similar to that of the pixel immediately previous to the intersecting portion. Furthermore, for example, the calculating function 109c determines a pixel as a pixel to be included in the route if the calculated difference is smaller than the threshold, and the pixel has a TDC similar to that of the pixel immediately previous to the intersecting portion, among the pixels with the TTP similar to that of the pixel immediately previous to the intersecting portion.

Explained in the first to the third embodiments described above is an example in which the calculating function 109c receives the designation of the predetermined position in a DSA image, but the embodiment is not limited to such an example. For example, the calculating function 109c may present to the operator various types of X-ray images such as an X-ray image with no background subtraction applied, or a color image resultant of the parametric imaging, and may receive the designation of the predetermined position on the presented X-ray image. It is possible for the calculating function 109c not to receive the designation of the predetermined position from the operator, and for the calculating function 109c to identify a group of pixels having a predetermined size in the DSA image as a nidus, and to automatically establish the junction point between the nidus and the blood vessel region as the predetermined position, for example.

Furthermore, explained in the first to the third embodiments is an example in which DSA images are generated by causing the acquisition function 109a to acquire X-ray images using a contrast agent, and causing the image generating function 109b to perform image processing to the X-ray images, and in which the route is calculated based on the generated DSA images, but the embodiment is not limited to such an example. For example, the calculating function 109c may calculate the route based on the temporal transition of the signal intensity in the blood vessel region in the X-ray images with no subtraction process applied by the image generating function 109b.

Furthermore, explained in the first to the third embodiments is an example in which the unit area consists of one pixel, but the unit area may be an area consisting of a plurality of pixels. For example, the calculating function 109c may calculate TTP for each unit area consisting of four pixels. To explain using an example, the calculating function 109c calculates the time required for the sum of signal intensities at four respective pixels, which make up the unit area, to reach the peak from a predetermined timing (e.g., the time at which the injection of the contrast agent into the blood vessel of the subject P has been started) as the TTP. The calculating function 109c can then calculate the route based on the continuity of the TTPs calculated for the respective unit areas. For example, the calculating function 109c sequentially compares the TTPs between the adjacent unit areas, using the unit area at the predetermined position R1 as a starting point, and calculates the route in a manner following the TTPs at the respective unit areas, retrospectively, in the blood vessel region. Furthermore, the image generating function 109b can generate a color image each pixel of which is reflected with color information based on the TTP, by assigning the TTP calculated for a unit area as the TTP at the pixels making up the unit area.

Explained in the embodiments is an example in which the X-ray diagnostic apparatus performs the processes described above, but the embodiment is not limited to such a configuration, and an image processing apparatus may be caused to execute the processes, for example. In such a configuration, the processing circuitry 109 is included in the image processing apparatus, and executes the processes described above.

The elements included in the apparatuses according to the first to the third embodiments are merely functional and conceptual representations, and are not necessarily need to be configured physically in the manner illustrated in the drawings. In other words, the specific configurations in which the apparatuses are distributed or integrated are not limited to those illustrated, and the whole or a part of such apparatuses may be functionally or physically distributed or integrated in any unit, depending on various loads or utilizations. Furthermore, the processing functions executed on each of the apparatuses may be, either entirely or partly, implemented as a CPU and a computer program parsed and executed by the CPU, or as a piece of hardware using a wired logic.

Furthermore, the control method explained in the first to the third embodiments may be implemented by causing a computer, such as a personal computer or a workstation, to execute a control program prescribed in advance. Such a control program can be distributed over a network such as the Internet. The control program may also be recorded in a computer-readable recording medium such as a hard disk, a flexible disk (FD), a compact disc read-only memory (CD-ROM), a magneto-optical disc (MO), and a digital versatile disc (DVD), and executed by being read by a computer from the recording medium.

According to at least one of the embodiment described above, the efficiency of a procedure using a blood vessel image can be improved.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus, comprising:
processing circuitry configured to:
acquire a plurality of X-ray images over time based on X-rays having passed through a subject injected with a contrast agent;
calculate an inflow path from among a plurality of blood vessels representing possible inflow paths by performing searching using a temporal transition of signal intensities of the injected contrast agent along the inflow path in a direction opposite a direction of blood flow, wherein the inflow path is a first blood vessel region of a path in the X-ray images traversed by the injected contrast agent leading to a predetermined position in a second blood vessel region in the X-ray images; and
perform control to display, on a display, the calculated inflow path of the first blood vessel region in a display mode that is different from that of a blood vessel region other than the inflow path.

2. The X-ray diagnostic apparatus according to claim 1, wherein the processing circuitry is further configured to:

calculate, for each unit area consisting of one or more pixels in the X-ray images, a feature quantity related to a flow of the injected contrast agent, based on the temporal transition of the signal intensities, and calculate the inflow path based on continuity of the calculated feature quantity.

3. The X-ray diagnostic apparatus according to claim 2, wherein the processing circuitry is further configured to:

use a unit area corresponding to the predetermined position as a starting point and sequentially compare feature quantities of adjacent unit areas, starting from the unit area corresponding to the starting point, and sequentially identify a unit area with a feature quantity that is temporarily previous, and calculate identified unit areas as the inflow path.

4. The X-ray diagnostic apparatus according to claim 2, wherein, when a third blood vessel region represented in the X-ray images has an intersecting portion in which blood vessels intersect with each other, the processing circuitry is further configured to calculate, for each unit area near the intersecting portion, an evaluation that is based on continuity of the feature quantity at the unit area and the feature quantity at a unit area immediately previous to the intersecting portion, and a positional relation between the unit area and the unit area immediately previous to the intersecting portion, and calculate the inflow path through the intersecting portion based on the calculated evaluation.

5. The X-ray diagnostic apparatus according to claim 4, wherein the processing circuitry is further configured to calculate the evaluation based on a direction of the inflow path to the unit area immediately previous to the intersecting portion.

6. The X-ray diagnostic apparatus according to claim 4, wherein the processing circuitry is further configured to calculate a plurality of feature quantities, calculate the evaluation based on the calculated feature quantities, and calculate the inflow path through the intersecting portion based on the calculated evaluation.

7. The X-ray diagnostic apparatus according to claim 4, wherein, when a difference between evaluations of respective unit areas near the intersecting portion is less than a predetermined threshold, the processing circuitry is further configured to determine a plurality of blood vessel regions corresponding to the inflow path, the blood vessel regions including the respective unit areas each having the evaluation.

8. The X-ray diagnostic apparatus according to claim 7, wherein the processing circuitry is further configured to receive an operation of selecting one of the calculated blood vessel regions corresponding to the inflow path.

9. The X-ray diagnostic apparatus according to claim 1, wherein the processing circuitry is further configured to calculate the inflow path through an intersecting portion in which blood vessels intersect with each other in the X-ray images acquired from a predetermined direction, by comparing the X-ray images with another plurality of X-ray images acquired from a direction that is different from the predetermined position.

10. The X-ray diagnostic apparatus according to claim 1, wherein, when a third blood vessel region in the X-ray images has an intersecting portion in which blood vessels intersect with each other, the processing circuitry is further configured to calculate a vector representing a movement of the injected contrast agent, for each unit area consisting of one or more pixels, in the third blood vessel region in the X-ray images, near the intersecting portion, by comparing the X-ray images with each other, and calculate the inflow path through the intersecting portion based on a similarity of the vectors in the respective unit areas.

11. The X-ray diagnostic apparatus according to claim 1, wherein, when the second blood vessel region in the X-ray images has an intersecting portion in which blood vessels intersect with each other, the processing circuitry is further configured to calculate the inflow path through the intersecting portion by performing computational fluid dynamics based on the X-ray images.

12. The X-ray diagnostic apparatus according to claim 1, wherein, when the second blood vessel region in the X-ray images has an intersecting portion in which blood vessels intersect with each other, the processing circuitry is further configured to calculate the inflow path through the intersecting portion based on similarity in the temporal transitions of the signal intensities of the injected contrast agent at respective unit areas each of which consists of one or more pixels, in the second blood vessel region in the X-ray images.

13. The X-ray diagnostic apparatus according to claim 2, wherein the feature quantity calculated by the processing circuitry is time required for the signal intensities to reach a peak from a predetermined timing, a peak signal intensity, or a cumulative sum of the signal intensities.

14. The X-ray diagnostic apparatus according to claim 1, wherein the processing circuitry is further configured to perform control to display the inflow path as a blood vessel image in a roadmap on the display, or display the X-ray images in which the inflow path is emphasized as a blood vessel image in the roadmap on the display.

15. The X-ray diagnostic apparatus according to claim 2, wherein the processing circuitry is further configured to:

generate a color image, each unit area of which is reflected with color information that is based on the feature quantity, and perform control to display the first blood vessel region corresponding to the calculated inflow path in the color image, as a blood vessel image in a roadmap, on the display.

16. The X-ray diagnostic apparatus according to claim 15, wherein the processing circuitry is further configured to perform control to display the first blood vessel region corresponding to the calculated inflow path in the color image, and the second blood vessel region in the X-ray image, as the blood vessel image in the roadmap, on the display.

17. The X-ray diagnostic apparatus according to claim 1, wherein the processing circuitry is further configured to:

receive a designation of the predetermined position in a color image in which each unit area consisting of one or more pixels in blood vessel regions represented in the X-ray images is reflected with color information that is based on the X-ray images or based on a feature quantity calculated based on the temporal transition of the signal intensity of the injected contrast agent in the X-ray images, and calculate the inflow path leading to the designated predetermined position.

18. An image processing apparatus, comprising:

processing circuitry configured to calculate an inflow path from among a plurality of blood vessels representing possible inflow paths by performing searching using a temporal transition of signal intensities of the injected contrast agent along the inflow path in a direction opposite a direction of blood flow, wherein the inflow path is a first blood vessel region of a path in the X-ray images traversed by an injected contrast agent leading to a predetermined position in a second blood vessel region in a plurality of X-ray images, and the X-ray images are acquired over time based on X-rays having passed through a subject injected with the injected contrast agent, and perform control to display, on a display, the calculated inflow path of the first blood vessel region in a display mode that is different from that of a blood vessel region other than the inflow path.

19. The image processing apparatus according to claim 18, wherein the processing circuitry is further configured to:

calculate, for each unit area consisting of one or more pixels in the X-ray images, a feature quantity related to a flow of the contrast agent, based on the temporal transition of the signal intensities, and calculate the inflow path based on continuity of the calculated feature quantity.

* * * * *